(12) United States Patent
McClain et al.

(10) Patent No.: US 12,702,786 B1
(45) Date of Patent: Aug. 11, 2026

(54) MODULATING SENSORY PERCEPTIONS DURING PSYCHEDELIC INDUCED THERAPY

(71) Applicant: Medda, Inc., Ira, MI (US)

(72) Inventors: Caleb McClain, Ira, MI (US); Jeffrey Humpherys, Lehi, UT (US); Mounir Bendahmane, Canton, MI (US)

(73) Assignee: Medda, Inc., Ira, MI (US)

( * ) Notice: Subject to any disclaimer, the term of this patent is extended or adjusted under 35 U.S.C. 154(b) by 995 days.

(21) Appl. No.: 17/875,506

(22) Filed: Jul. 28, 2022

Related U.S. Application Data

(60) Provisional application No. 63/226,421, filed on Jul. 28, 2021.

(51) Int. Cl.
*A61M 21/00* (2006.01)

(52) U.S. Cl.
CPC . *A61M 21/0094* (2013.01); *A61M 2021/0016* (2013.01); *A61M 2021/0027* (2013.01); *A61M 2021/0044* (2013.01); *A61M 2202/0007* (2013.01); *A61M 2205/05* (2013.01); *A61M 2205/507* (2013.01)

(58) Field of Classification Search
CPC .. A61M 21/00; A61M 21/0094; A61M 21/02; A61M 2021/0005; A61M 2021/0016; A61M 2021/0022; A61M 2021/0027; A61M 2021/0044; A61M 2021/005
See application file for complete search history.

(56) References Cited

U.S. PATENT DOCUMENTS

2020/0219615 A1* 7/2020 Rabin .................... G16H 20/00

* cited by examiner

*Primary Examiner* — Carrie R Dorna

(57) ABSTRACT

The present invention extends to methods, systems, and computer program products for modulating sensory perceptions during psychedelic induced therapy. Remote distributed virtual environments can be created enabling virtual group psychedelic therapy. Visual, auditory, and olfactory devices can be used to alter a patients' baseline sensory perceptions and obfuscate or limit knowledge about whether a patient was in the treatment or control group within placebo-controlled clinical trials. Various mechanisms are used to administer psychedelic drugs to a patient and accumulate psychedelic drugs in specific areas of the brain. Virtual environments can be tailored and specific brain wave states induced enabling targeted therapeutic outcomes in psychedelic therapy.

17 Claims, 2 Drawing Sheets

MODULATING SENSORY PERCEPTIONS DURING PSYCHEDELIC INDUCED THERAPY

CROSS-REFERENCE TO RELATED APPLICATIONS

This application claims the benefit of U.S. Provisional Patent Application Ser. No. 63/226,421, entitled "Modulated Sensory Perceptions During Psychedelic Induced Therapy", filed Jul. 28, 2021, which is incorporated herein in its entirety.

BACKGROUND

1. Background and Relevant Art

Psychedelic treatments may be effective in the treatment of several mental health and neurological conditions, including but not limited to major depressive disorder (MDD), generalized anxiety disorder (GAD), post-traumatic distress disorder (PTSD), etc.

There are at least two limitations in obtaining clinical knowledge associated with psychedelic research. One limitation is that blinded placebo-controlled psychedelic drug trials are nearly impossible to implement, since the presence or absence of the distinct psychophysical effects of the drug(s) may signal to the patient whether he or she were in the treatment group or the control group. Further, while recent studies are showing remarkable outcomes from the use of psychedelics for several mental health and neurological conditions, there are a few documented cases where patients have had bad reactions to psychedelic treatment. There is some indication that these side effects can be mitigated in a clinical setting.

BRIEF SUMMARY

Examples extend to methods, systems, and computer program products for modulating sensory perceptions during psychedelic induced therapy. Remote Distributed Virtual Environments (DVE) can be created enabling virtual group psychedelic-assisted therapy. Visual, auditory, and olfactory devices can be used to alter a patients' baseline sensory perceptions and obfuscate or limit knowledge about whether a patient was in the treatment or control group within placebo-controlled clinical trials. Various mechanisms are used to administer psychedelic drugs to a patient and accumulate psychedelic drugs in specific areas of the brain. Virtual environments can be tailored enabling targeted therapeutic outcomes in psychedelic therapy. Sensory modulation and/or deprivation can be used during psychedelic therapy.

Natural language processing and/or machine learning models can gather and analyze data related to psychedelic drug research and therapy. Dynamic experience and effects of modulating various elements of sensory perception during psychedelic therapy can be quantified.

More specifically, in one aspect, a participant/patient meets with clinicians to determine appropriate drugs and care pathway. The clinicians supervise a series of baseline analysis of the participant/patient to assess the participant/patient's current health. Participant/patient and clinician can conduct psychological preparation during the days/weeks prior to an VR/AR psychedelic therapy session(s). Simulations can be selected, planned, staged, designed per participant/patient's needs/goals.

Participant/patient attends VR psychedelic drug therapy session. Clinicians prepare room, materials, and participant/patient begins session. Equipment is connected and headset secured on participant/patient head/face. If/when appropriate, microbubbles are injected intravenously. A psychoactive agent or drug is administered to the Participant/patient (e.g., via intranasal, intravenously, inhalation, oral ingestion). Simulations can be commenced and timed to calculated/observed drug onset of action. Participant/patient engages in virtual environment, completes tasks, and interacts within DVE group.

Clinicians manage session, engage in guidance methods and/or psychotherapy. Clinicians taking record, monitoring recording equipment, ID peak of action.

Simulation(s) can be timed to deliver climax of sensory modulation during peak of drug action. Sensory modulation(s) (e.g., visual, auditory, olfactory) continues for duration of drug action. Clinicians observe and record various data points. Clinicians observe, determine drug action termination. Participant/patient verbally confirms drug action termination. Clinicians end simulations and/or sensory modulation, remove headset. Participant/patient and Clinician engage in post-therapy processing session & evaluation. Session ends.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by practice. The features and advantages may be realized and obtained by means of the instruments and combinations particularly pointed out in the appended claims. These and other features and advantages will become more fully apparent from the following description and appended claims, or may be learned by practice as set forth hereinafter.

BRIEF DESCRIPTION OF THE DRAWINGS

In order to describe the manner in which the above-recited and other advantages and features can be obtained, a more particular description will be rendered by reference to specific implementations thereof which are illustrated in the appended drawings. Understanding that these drawings depict only some implementations and are not therefore to be considered to be limiting of its scope, implementations will be described and explained with additional specificity and detail through the use of the accompanying drawings in which.

DETAILED DESCRIPTION

Figure 1A:
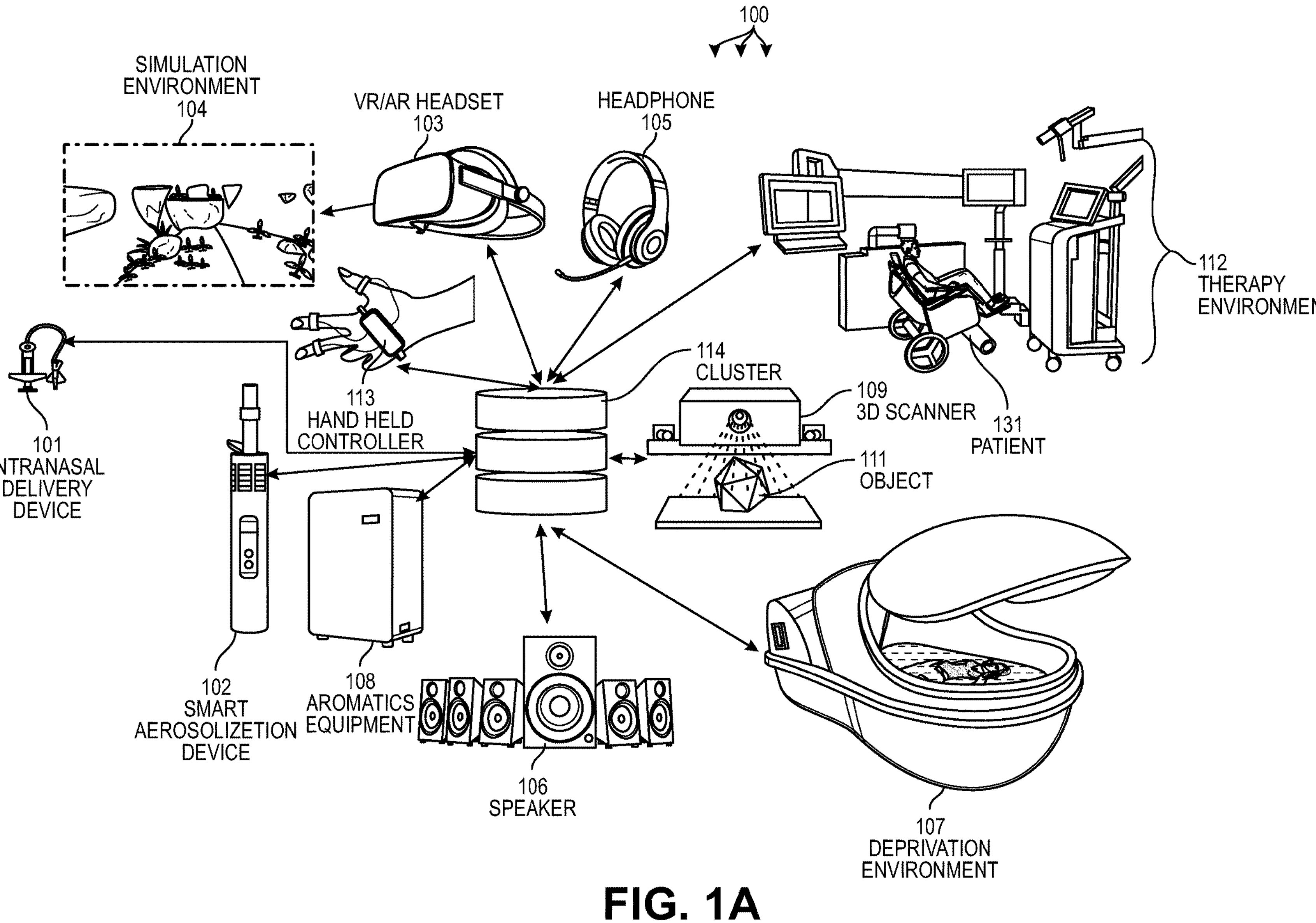
FIG. 1A depicts an example architecture that facilitates psychedelic assisted therapy.

Examples extend to methods, systems, and computer program products for modulating sensory perceptions during psychedelic induced therapy.

Aspects of the invention use sensory altering devices and experiences to augment or modulate a psychedelic treatment. The invention has many applications. One application is to alter patients' baseline sensory perception in a way that could obfuscate or limit knowledge about whether a patient was in the treatment group or the control group, particularly in a low dose setting. Another application of sensory altering devices and experiences is to help guide the psychedelic treatment experience (both in trials and as a standard of care), for example, in a way that could help regulate the patient experience to enhance positive effects and avoid adverse effects.

The invention facilitates, by simulating a psychedelic experience, an ability to examine the tangible effects of the simulation as a potential stand-alone digital therapeutic pathway. Further, the invention provides clinicians and researchers mechanisms to effectively modulate the various stimuli to target specific therapeutic outcomes.

There are at least three systems that regulate human sensory perception: the visual system, the vestibular system, and the golgi tendon apparatus. The stimulation and/or augmentation of one's sense of balance and spatial orientation—either one in isolation or both in concert—can provoke euphoria, hallucinations, vertigo, delirium, etc.

Virtual reality (VR) systems can stimulate, modify, and augment a human visual system. A patient (or other user) can wear virtual reality glasses (or goggles) and be presented with different visual stimuli that could alter his or her state of perception. Presenting different visual stimuli can decrease the likelihood of a patient (or other user) learning if he or she has been assigned to a psychedelic treatment group or a placebo control group. For example, stimuli presented to a patient in simulated environment can be used to obfuscate knowledge of whether a patient is in a control or drug arm of a clinical trial (e.g., placebo-by-proxy).

Furthermore, the visual stimulus can help guide patient (or other user) toward happier thoughts and experiences during treatment and help steer him or her away from bad memories or experiences that are related to the underlying mental health condition (e.g., abuse, trauma). In the same way that soothing music can help someone improve quality of sleep and dreams, VR systems can guide the psychedelic experience. One study found that non-psychedelic induced "Prolonged Exposure" VR therapy reduced PTSD symptoms by an average of fifty percent, and it disqualified over seventy-five percent of participants for PTSD after treatment.

Noise cancelling headphones can be used to stimulate, modify, and augment a human vestibular system. Noise canceling headphones can introduce specific sonic frequencies to generate pathological fluid-mechanical waves and further simulate substance-induced states of consciousness. For example, sonic frequencies can be introduced to simulate various aspects of psychophysical responses commonly attributed to psychedelic experiences.

A golgi tendon apparatus can be used can be used to alter a patient (or other user's) perception. For example, an isolation or deprivation tank or room can be used in concert with VR and/or Augmented Reality (AR) systems to facilitate altering a patient's (or other user's) perception baseline and correspondingly the patient's ability to detect whether he or she had been assigned to a psychedelic treatment group or a placebo control group.

Aspects of the invention provide a system capable of tailoring simulated environments to induce specific psychophysical responses in participants. By personalizing simulated physical environments, participants can be presented with scenarios wherein aspects of past traumatic experiences can be reprocessed during an induced psychedelic therapy. During the experience, the normal perception of the participant is altered and he or she is exposed to a simulated reconstruction of a past, traumatic event. This presents a unique opportunity (through a combination of VR/AR simulation, altered state of consciousness and behavioral therapy) to form new perceptions of past traumatic events or aspects of the mental health indication associated with those events. Aspects of the invention can be used to assist a human with processing various conditions, including various major depressive disorders, PTSD, OCD, ADD/ADHD, social or general anxiety, phobias, autism, and others.

Aspects of the invention also provide participants the ability to interact with simulated environments. Similar to experiences with VR/AR games, participants in the VR/AR psychedelic experience can interact with problem solving scenarios, or other environments and scenarios, in which they can make decisions that affect the progression of their simulated experience. Through this interaction with the simulation, clinicians can evaluate a participant's cognitive processing of the conditions, problems or scenarios. Observation of this cognitive process, and data generated thereby, can inform clinicians as to various aspects of the participant's current state of awareness, assess progress and therapeutic impact, as well as gain insight that may not be available or accurate via participant sentiment alone.

Aspects of the invention can be implemented in distributed virtual environments (DVEs). Within a DVE, users can interact with objects and other participants, thereby causing changes to the states of those simulated objects or other participants' sensory experiences. These state change events are transmitted to other users within the environment across a network or internet connection using data connection and transfer mechanisms including but not limited to, Wireless Local Area Network (WLAN), Local Area Network (LAN), Wide Area Network (WAN), Bluetooth, 5G, etc. Patients can remotely participate in interactive therapy and/or group therapy simulations using a DVE.

As such, clinicians are provided an opportunity to create 3D models of physical objects, which can then be included in simulated environment(s). The simulated object can provide participants a "psychological anchor", intended to disarm or comfort them during psychedelic therapy. The presence of a familiar object can serve to further reduce the potential for confusion, overwhelming recollections of trauma, mania, psychotic episodes, or otherwise negative responses to the simulation or drug therapies.

Soundscapes and/or specific sonic frequencies, for example, isochronic or binaural tones, can be used to induce specific brain wave states in participants. There are several types of brain waves including Gamma, Beta, Alpha, Theta, Delta. Each brainwave type is associated with a frequency range and a mental state. Modulating the brain wave state of the participant induces various states of consciousness, or psychophysical responses, which can be tailored to support predictable and repeatable therapeutic outcomes.

Aspects of the invention can also facilitate Augmented Synergistic Therapy. Augmented Synergistic Therapy includes targeting of psychedelic substances at specific areas of the brain using intravenously injected microbubbles (which could be injected into a blood vessel elsewhere, such as in the arm, for example), together with focused ultrasound directed at the brain region to be targeted. The psychedelic drug is administered via oral ingestion, inhalation, intranasal administration, or IV injection. The ultrasound causes the microbubbles to oscillate, which expands and contracts the blood vessels and the perivascular space surrounding the blood vessels. Blood vessel expansion/contraction allows/causes the drug to penetrate through the perivascular space, resulting in local accumulation of the drug at the ultrasound-targeted region.

Additionally, olfactory stimulation can be facilitated by introducing various aromatics during a psychedelic, or simulated psychedelic, therapy session. Stimulating the olfactory cortex serves to further induce psychophysiological responses originating at various regions of the brain. The distribution of this signaling can be tailored to affect specific hormonal and neurotransmitter responses, presenting an additional dimension to therapy protocols.

Natural Language Processing or vocal processing tools can be utilized to capture and generate structured data from patient sentiment during a psychedelic therapy. As such, clinicians can observe data related to vocal consistencies and variance of sentiment, which may provide insight into the effects of these substances on the brain region responsible for speech.

Aspects further include a layered method for full-sensory augmentation, a strategy to personalize experiences, and use of technologies that facilitate such a dynamic methodology. In the time leading up to the therapy session(s), participants meet with clinicians for pre-therapy assessment screening. As part of pre-therapy assessment screening, a participant can bring a physical object, specifically, an object which induces a positive or negative emotional response for the participant. Objects are placed in the 3D modelling device and scanned to generate a simulation of the objects. Simulated objects can then be included within a simulated environment or program.

In a sound-isolated or sensory deprivation pod or room, a participant is fitted with virtual reality eyewear, which is then linked to a compute cluster containing software and simulated physical environments or visual aspects of a psychedelic experience, such as, visual hallucinations. The participant is also fitted with high-fidelity ear wear, used to generate a sonic (and potential audible) component and/or to modulate inner-ear pressure. An IV line or port is started, and the ultrasound equipment is directed at a specified region of the participant's brain. The psychedelic substance(s) are administered, and the microbubbles are injected via IV. The simulated visual, sonic, and aromatic components are engaged, and the psychological treatment begins.

Unmitigated environmental and psychological variables may present a risk for patients and clinicians, both during and after psychedelic therapy. A psychedelic substance itself is merely the chemical catalyst, whereby its effects open the mind and free the nervous system of its ordinary perception of patterns, structures, construct, and circumstances. The nature and outcome of the experience depends, almost entirely, on what is commonly referred to as "Set and Setting", where "set" refers to the participant's mindset, and "setting" refers to the participant' physical and social surroundings and environment during the chemically-induced experience. Inconsistencies in set and/or setting can be (potentially highly) detrimental to the psychedelic experience, the intended outcome, and the behavioral, psychophysical, or psychological effects thereof.

Implementations can comprise or utilize a special purpose or general-purpose computer including computer hardware, such as, for example, one or more computer and/or hardware processors (including any of Central Processing Units (CPUs), and/or Graphical Processing Units (GPUs), general-purpose GPUs (GPGPUs), Field Programmable Gate Arrays (FPGAs), application specific integrated circuits (ASICs), Tensor Processing Units (TPUs)) and system memory, as discussed in greater detail below. Implementations also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations can comprise at least two distinctly different kinds of computer-readable media: computer storage media (devices) and transmission media.

Computer storage media (devices) includes RAM, ROM, EEPROM, CD-ROM, Solid State Drives ("SSDs") (e.g., RAM-based or Flash-based), Shingled Magnetic Recording ("SMR") devices, Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

In one aspect, one or more processors are configured to execute instructions (e.g., computer-readable instructions, computer-executable instructions, etc.) to perform any of a plurality of described operations. The one or more processors can access information from system memory and/or store information in system memory. The one or more processors can (e.g., automatically) transform information between different formats, such as, for example, between any of: care pathways, psychoactive agent/drug indications, psychoactive agent/drug administrations, distributed virtual environments (DVEs), simulated environments, simulated objects, digitized scanned objects, visual sensory stimuli, auditory sensory stimuli, olfactory sensory stimuli, NLP models, ML models, recorded audio/video, handheld controller inputs, smart aerosolization device commands, medical equipment commands, etc.

System memory can be coupled to the one or more processors and can store instructions (e.g., computer-readable instructions, computer-executable instructions, etc.) executed by the one or more processors. The system memory can also be configured to store any of a plurality of other types of data generated and/or transformed by the described components, such as, for example, care pathways, psychoactive agent/drug indications, psychoactive agent/drug administrations, distributed virtual environments (DVEs), simulated environments, simulated objects, digitized scanned objects, visual sensory stimuli, auditory sensory stimuli, olfactory sensory stimuli, NLP models, ML models, recorded audio/video, handheld controller inputs, smart aerosolization device commands, medical equipment commands, etc.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, in response to execution at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Aspects of the invention may be practiced in network computing environments with many types of computer system configurations, including, personal computers, desktop computers, laptop computers, message processors, handheld devices, wearable devices, multicore processor systems, multi-processor systems, microprocessor-based or programmable consumer electronics, network PCs, minicomputers, mainframe computers, mobile telephones, PDAs, tablets, routers, switches, smart vaporizing devices, computational clusters, databases, and the like. The described aspects may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more Field Programmable Gate Arrays (FPGAs) and/or one or more application specific integrated circuits (ASICs) and/or one or more Tensor Processing Units (TPUs) can be programmed to carry out one or more of the systems and procedures described herein. Hardware, software, firmware, digital components, or analog components can be specifically tailor-designed for a higher speed processing or artificial intelligence that can enable processing. In another example, computer code is configured for execution in one or more processors, and may include hardware logic/electrical circuitry controlled by the computer code. These example devices are provided herein purposes of illustration, and are not intended to be limiting. Embodiments of the present disclosure may be implemented in further types of devices.

The described aspects can also be implemented in cloud computing environments. In this description and the following claims, "cloud computing" is defined as a model for enabling on-demand network access to a shared pool of configurable computing resources. For example, cloud computing can be employed in the marketplace to offer ubiquitous and convenient on-demand access to the shared pool of configurable computing resources (e.g., compute resources, networking resources, and storage resources). The shared pool of configurable computing resources can be provisioned via virtualization and released with low effort or service provider interaction, and then scaled accordingly.

A cloud computing model can be composed of various characteristics such as, for example, on-demand self-service, broad network access, resource pooling, rapid elasticity, measured service, and so forth. A cloud computing model can also expose various service models, such as, for example, Software as a Service ("SaaS"), Platform as a Service ("PaaS"), and Infrastructure as a Service ("IaaS"). A cloud computing model can also be deployed using different deployment models such as private cloud, community cloud, public cloud, hybrid cloud, and so forth. In this description and in the following claims, a "cloud computing environment" is an environment in which cloud computing is employed.

Architecture

Various aspects of the invention can include any of: a smart aerosolization/nebulizer device, interactive VR/AR software, simulated environment programs, a VR/AR headset, high definition projector and screen, noise canceling (e.g., surround sound) headphones, a speaker system, sound isolated, sensory deprivation tank or room, isochronic or binaural audio compositions, aromatic equipment, scent diffusers, a 3D modeling scanner, biomedical monitoring equipment, ultrasound equipment, a magnetic resonance imaging (MRI) machine, Intravenous (IV) equipment, microbubbles suspension, audio/video (A/V) recording equipment, Natural Language Processing (NLP) models, Machine Learning (ML) models, handheld controllers, a computation system (e.g., a computing cluster), network (e.g., Internet) connections.

Aspects of the invention can utilize an intranasal delivery device configured to administer drugs through an intranasal spray. Using an intranasal device with intranasal spray facilitates drug delivery directly to the brain along the trigeminal and olfactory nerves via neuronal receptors at the trigeminal and/or olfactory nerves. Administration via nerves directly to the brain provides unique access to penetrate the blood-brain barrier, and may be utilized to optimize drug delivery and maximize, prolong, or modulate the activity or effectiveness of psychedelic substances.

An intranasal delivery device can be a smart aerosolization/nebulizer device. Delivery using a smart aerosolization/nebulizer device provides advantageous drug absorption characteristics, for example, by targeting delivery to the highly-vascularized respiratory mucosa, large absorptive surface area, thin air-blood barrier, low enzymatic activity in the lung. For systemically acting drugs, the absorption profile of the drug from the lung may determine the onset, intensity, and duration of action of the drug. A smart aerosolization/nebulizer device can include a lithium ion battery, vaporization chamber, heating element, mouthpiece, and various semiconductors and microcontrollers necessary to heat materials to aerosolization whereby participants administer the nebulized or aerosolized material(s) via inhalation. A smart aerosolization/nebulizer device can be remotely monitored and controlled by software applications stored and launched from an external device, such as, a mobile phone and/or computational device or "cluster".

Substances, including both naturally occurring and synthetically produced compounds, which are pharmacologically classified or considered psychoactive and/or hallucinogenic in humans can be delivered. Substances can be delivered to participants/patients intranasally, orally or intravenously in controlled environments. Delivered substances can include but are not limited to psilocin, psilocybin, 5 MEO-DMT, N, N-DMT, Baeocystin, nor-Baeocystin, Aeruginascin, Ibogaine, Voacangine, Lysergic Acid Amide, Lysergic Acid Diethylamide (LSD), Mescaline, Ketamine, 3,4-Methylenedioxyamphetamine (MDA, MDMA), 2C family drugs, 3C family drugs, Harmaline, Salvinorin A, Salvinorin B methoxymethyl ether, Salvinorin B ethoxymethyl ether, etc. Additionally, drugs from classes including but not limited to Indoles, Tryptamines, Ibogoids, Ergolines, Phenethylamines and alkoxylated phenethylamines, Substituted phenethylamines, Indane derivatives, Benzocyclobutene derivatives, NBOMe derivatives, NBOH derivatives, NBMD derivatives, NBF derivatives, Substituted amphetamines (alpha-methyl-phenethylamines), Phytocannabinoids, Synthetic cannabinoids, may be extracted from raw material sources including but not limited to plants, roots, aerial parts, branches, fungi, ergot, and other naturally occurring sources. These substances may also be synthesized or biocatalyzed, or chemically converted from other base materials. Many materials can be additionally refined, purified, or optimized in stages including but not limited to distillation, isolation, lyophilization, liposomization, emulsification, or microfluidics to render, prepare, and/or optimize the substances for human bioavailability and consumption. The material is prepared into a form factor or packaged into a delivery device designed for administering the drug in humans.

These types of substances affect the patients' neural coupling and perception in unique ways. As part of a therapy protocol, these substances induce perceptual changes that provide unique potential across a range of mental health conditions. Upon administration, these substances induce hallucinations, perceptual anomalies, and/or other substantial subjective changes in thought, emotion, and consciousness. In contrast to the use of conventional psychiatric medication that is taken by the patient either regularly or as-needed, psychedelic therapy patients remain in an extended psychotherapy session during the acute activity of a psychedelic drug. Psycholytic therapy involves the use of low to medium doses of psychedelic drugs, repeatedly at intervals of 1-2 weeks, where Psychedelic therapy involves the use of very high doses of psychedelic drugs, with the aim of promoting transcendental, ecstatic, religious or mystical peak experiences. A trained professional can remain with a participant/patient when under the influence of a psychedelic drug.

Virtual reality therapy (VRT), or virtual reality immersion therapy (VRIT), uses computer programs designed, in concert with wearable visual devices, to immerse participants within artificially created environments. VRT or VRIT can give participants/patients simulated experiences used to diagnose and treat psychological conditions. A participant/patient accesses a computer-simulated world. The computer simulated world presents perceptual stimuli to the participant/patient. In turn, the participant/patient can manipulate elements of the modeled world and thus experience a degree of presence. Participants/patients can safely interact with simulations of traumatic events or phobias, without the inherent danger of the traumatic events associated with phobias themselves.

Simulated experience technology can especially useful for exposure therapy, where patients/participants are exposed to recreations of traumatic stimuli inside these virtual environments. Modeled environments and their rules may draw from reality or may be purely simulated. Examples of environments may include but are not limited to; automobile/airplane interior, forests, mountains, valleys, beaches, cities, boat deck, or obscure otherworldly environments. Examples of rules within simulations include gravity, topography, locomotion, real-time actions, and communication.

Specialized imagery can be presented during a psychedelic substance induced therapy. Visualizations, visual objectives, and problem-solving scenarios are played during the psychedelic virtual reality experience. The same or similar visualizations, visual objectives, and problem-solving scenarios are replayed later while participants are engaged with the virtual reality experience, but have not ingested psychedelic substances. The present invention can (potentially dramatically) lower activity in the default mode network, which is associated with the generation of a sense of self, during a psychedelic therapy experience and during the repeated VR visualizations. The use of VR also enables experimenters to establish control groups for tests of the therapeutic efficacy of psychedelic experiences by recreating the environment users might expect to experience while under the influence of psychedelics.

A Virtual Reality (VR) headset is a head-mounted device that provides virtual reality for the wearer. VR headsets are widely used with video games, but they are also used in other applications, including simulations (e.g., for training purposes) and psychotherapy. A virtual reality headset can include a stereoscopic head-mounted display (providing separate images for each eye), stereo sound, and head motion tracking sensors (which may include gyroscopes, accelerometers, magnetometers, structured light systems or eye tracking sensors). VR headsets can use head-tracking, which changes the field of vision as a person turns his or her head. The lenses of the headset can map the up-close display to a wide field of view, while also providing a more comfortable distant point of focus.

Alternately, a (e.g., high-definition) projector and screen can be used to visually simulate an environment.

Speakers or headphones capable of virtual spatial audio (including but not limited to 5.1, 7.1, 10.2, 11.1, Dolby Atmos, THX) can be used to simulate sound moving in 3-dimensional spaces. Headphone systems with noise-cancelling capabilities reduce ambient noise which may interfere with the overall simulation and could create distractions for participants during therapy. Reducing or negating ambient noise and presenting surround sound enables participants to more fully immerse in simulations, and the desired effects of the therapy can be better realized An isolation room or tank can be utilized to eliminate as many potential stimuli of external senses as possible. A room with special insulation prevents external sounds from passing into the room where psychedelic therapy is underway. Sensory deprivation, sometimes called floatation or isolation therapy, includes a tank filled with water and salt solution that eliminates the brain's need to navigate gravity. In a light-free, sound-resistant, zero-gravity environment, the mind can redirect its thoughts and focus inward.

In a float tank, sight and sounds are removed, with the exception of the VR headset and/or downward facing LED screen displaying the virtual reality simulation. The air and water are also heated to skin temperature, so it becomes more difficult for a participate/patient to determine where their skin ends, and the water begins. Floating in a tank creates optimized conditions for removing external stimuli.

Using functional magnetic resonance imaging (fMRI), researchers at Laureate Institute for Brain Research studied 24 healthy volunteers before and after three weekly 90-minute float sessions. The results demonstrated that flotation- REST reduced statistical dependencies or functional connectivity during the resting state within and between brain regions involved in mind-wandering (the default mode network or DMN). Decreased activity of the DMN has also been linked to meditation and psychedelics by other studies.

Isochronic tones are regular beats of a single tone that are used alongside monaural beats and binaural beats in the process called brainwave entrainment. At its simplest level, an isochronic tone is a tone that is being turned on and off rapidly. Isochronic tones can create sharp, distinctive pulses of sound. A binaural beat is an auditory illusion perceived when two different pure-tone sine waves, both with frequencies lower than 1500 Hz, with less than a 40 Hz difference between them, are presented to a listener dichotically (one through each ear). Hypothesized benefits of binaural beats therapy can include: reduced stress, reduced anxiety, increased focus and concentration, increased motivation, increased confidence, and deeper meditation.

Brainwave synchronization and neural entrainment, refers to the hypothesized capacity of the brain to naturally synchronize its brainwave frequencies with the rhythm of periodic external stimuli, most commonly auditory, visual, or tactile. It is believed that patterns of neural firing, measured in Hz, correspond with states of alertness, such as, focused attention, deep sleep, etc. It is hypothesized that by listening to these beats of certain frequencies, one can induce a desired state of consciousness that corresponds with specific neural activity, such as, studying, sleeping, exercising, meditating, doing creative work, and so on. To induce the various brainwave states, these patterns and frequencies are designed in accordance with EEG measurements. A raw EEG can be described in terms of frequency bands: Gamma greater than 30 (Hz), Beta (13-30 Hz), Alpha (8-12 Hz), Theta (4-8 Hz), and Delta (less than 4 Hz). The depth of the modulation can be designed to reinforce the effectiveness of the psychedelic substances.

Aromatherapy is based on the usage of aromatic materials, including essential oils and other aroma compounds, with claims for improving psychological or physical well-being. Neuromodulation exists in the olfactory system and is responsible for neural plasticity and behavioral change in humans. The amygdala, a complex set of nuclei situated in the temporal lobe, lies beneath the primary olfactory cortex. The amygdala is involved in the formation of memories of emotional experiences, particularly those associated with fear, flight, and defense. Introducing aromatic profiles during a psychedelic-assisted therapy session may provide another manner to further target or tailor the psychedelic-assisted therapy.

A 3D model scanner (a desktop-sized device) can be used to digitize physical objects and render high resolution, digital simulations of objects. The digitally simulated objects can then be included within simulated environments. Participants in the psychedelic therapy may benefit from having a familiar object perceived as present during the experience, specifically, an object which induces a strong emotional response for the participant.

A 3D model scanner can use laser triangulation, white light or structured light technology, or infrared Vertical-Cavity Surface-Emitting Laser (VCSEL) structured light technology to scan real-life objects in three dimensions. After scanning, the simulated 3D object can be placed within a simulated environment program. Within a simulation, visual distortions can reduce the realism of the experience. The reduction of realism may result in reduced immersion, which can impact the efficacy of the therapy. As such, when presenting a simulated 3D object, or virtual artifacts, aspects of the invention can reduce visual distortions the greatest extent possible so as to preserve perceived object(s) realism during the psychedelic therapy experience.

Sensors, electrodes, and other neural monitoring equipment (including but not limited to fMRI, MRI, EEG) can be utilized by clinicians before, during, and after augmented psychedelic therapy. Monitoring can provide a baseline of a participant's/patient's neural activity and correspondingly the participant's/patient's "normal" brain activity. The sensors, electrodes, and other neural monitoring equipment can also be used to monitor the participant/patient during psychedelic therapy as well as at various times after psychedelic therapy. Comparisons can be made between neural activity monitored at different times. Through comparisons a clinician can determine the effects on brain activity caused by an augmented reality-aided psychedelic therapy protocol.

Focused ultrasound (FUS) equipment can target sound waves to a selected brain region through the skull. FUS can include an array of focused emitters used to perform real-time magnetic resonance imaging and thermograph. Moderate-intensity FUS has the potential to safely open the blood-brain barrier for localized delivery of therapeutics, while low levels of sonic energy can be used as a form of neuromodulation. FUS solutions may provide increased passage of psychedelics through the blood-brain barrier, as well as targeting substances at selected brain regions. FUS in combination with IV injections of microbubbles can be used to direct substances to regions of the brain not accessible with current delivery systems and methods.

Magnetic resonance imaging (MRI) may also be incorporated and combined with the microbubbles injection and FUS. Using MRI in combination with microbubbles and FUS can increase intensity and/or accuracy of targeting brain tissue.

IV equipment can be used for intravenous administered drugs or microbubble suspension.

In concert with FUS directed at specific brain regions designated for treatment, microbubbles containing a drug are injected intravenously into a participant/patient. FUS can cause the microbubbles to oscillate, which expands and contracts the blood vessels and the perivascular space surrounding the blood vessels. Blood vessel expansion/contraction, allows the drug to penetrate through the perivascular space, resulting in local accumulation of the drug at the ultrasound-targeted region.

A/V recording equipment can be used to record therapy sessions. Recordings give direct, factually correct representations of a therapy session which cannot be matched by the common, indirect method in supervision of recollection. Recordings facilitate the close examination of process and technique. Discrepancies between the recollected account of participants during psychedelic therapy and the recordings can be highlighted. Noting discrepancies serves the purpose of adapting the methodologies of the therapist, as well as document phenomena that have meaning and significance. Recordings may be later analyzed using ML models and/or NLP models, to detect anomalous details or elements potentially uncaptured by the attending therapist. Noting discrepancies also provides a mechanism to analyze subtle variations in vocal patterns (e.g., using ML models and/or NLP models) not otherwise detectable by human analysis alone.

Models in speech recognition can conceptually be divided into acoustic models and language models. Acoustic models can be used to transform sound signals into some kind of phonetic representation. Language models can use knowledge of words, grammar, and sentence structure for the language to recognize language meaning. Acoustic models and language models can be implemented with probabilistic models using ML algorithms.

Systems using this combination of models may prove effective in decoding unexpected sentence structures, as those structures can be instantaneously compared to a participant's baseline vocal structures, patterns, and phonetic groupings or a "lexicon". The ability to quickly compare patterns using NLP or ML may provide insights into the participants' cognitive changes which take place during a psychedelic therapy. For example, specific vocal, semantic, and/or behavioral patterns may be present in human participants during psychedelic induced experiences. Combined model systems can be used to detect these specific vocal, semantic, and/or behavioral patterns.

Handheld units can be used by participants/patients in a simulated environment and integrated into psychedelic therapy. Handheld units can feature an analog stick, buttons, triggers, and a system for detecting hand or finger gestures. Handheld units can allow a participant to interact with the simulated environment or other participants within the simulated environment, permitting a participant to directly influence a simulation. Simulated tactile interaction can take into account modalities designed to empower the participant/patient or reinforce the perceived safety of certain elements of the simulation and what it represents.

By allowing participants/patients a tactile control of elements in the therapy, participants/patients may find they are able to more effectively acclimate to the simulation and develop a heightened trust for the simulated surroundings. A handheld controller can also be used by participants/patients to perform/complete task-based interactions and/or make selections of simulation parameters, for example, touching, selecting, or holding virtual objects (including objects 3D scanned into a simulation).

Simulated environment programs and Distributed Virtual Environments (DVE) can be stored on a cluster where they can be accessed and enabled for use. A cluster can include a set of computers and/or other computing devices that work together to implement aspects of the invention.

Video, sounds, virtual objects & environments, as well as data collected during therapy sessions can be stored in databases in the cluster. Data, programmed objects, and environments may be accessed from the cluster remotely via an internet or network connection, using a headset (or projector and screen) to display the virtual environment. A network connection can include but is not limited to, Wireless Local Area Network (WLAN), Local Area Network (LAN), Wide Area Network (WAN), Bluetooth, wi-fi, D2D 5G, LTE, etc. providing connectivity between devices and a computational cluster and within the computational cluster.

In general, clinicians can utilize the described components to facilitate psychedelic assisted therapy sessions through simulated environments. In some psychedelic therapy sessions, therapists or psychiatrists are nondirective and support the participant/patient in exploring their inner experience. Using aspects of the invention, therapists or psychiatrists can utilize nondirective and support approaches and/or can also direct participants/patients toward aspects of a simulation designed to support therapeutic outcomes. Participants/patients can participate in psychotherapy pre-screenings before the psychedelic drug-induced therapy session. Based at least in part on pre-screening results, clinicians prepare participants/patients for the experience, guide them through the virtual or augmented reality assisted psychedelic experience, and continue therapy after the drug psychotherapy to support the integration of their experiences with the drug.

FIG. 1A depicts an example architecture 100 that facilitates psychedelic assisted therapy. As depicted, FIG. 1 includes intranasal delivery device 101, smart aerosolization device 102 (defined to include nebulizers), VR/AR headset 103, simulated environment 104, headphones 105 and/or speakers 106, sensory deprivation environment 107, aromatics equipment 108, 3D modelling scanner 109, object 111, therapy environment 112, handheld controller 113, cluster 114, and patient 131.

Figure 1B:
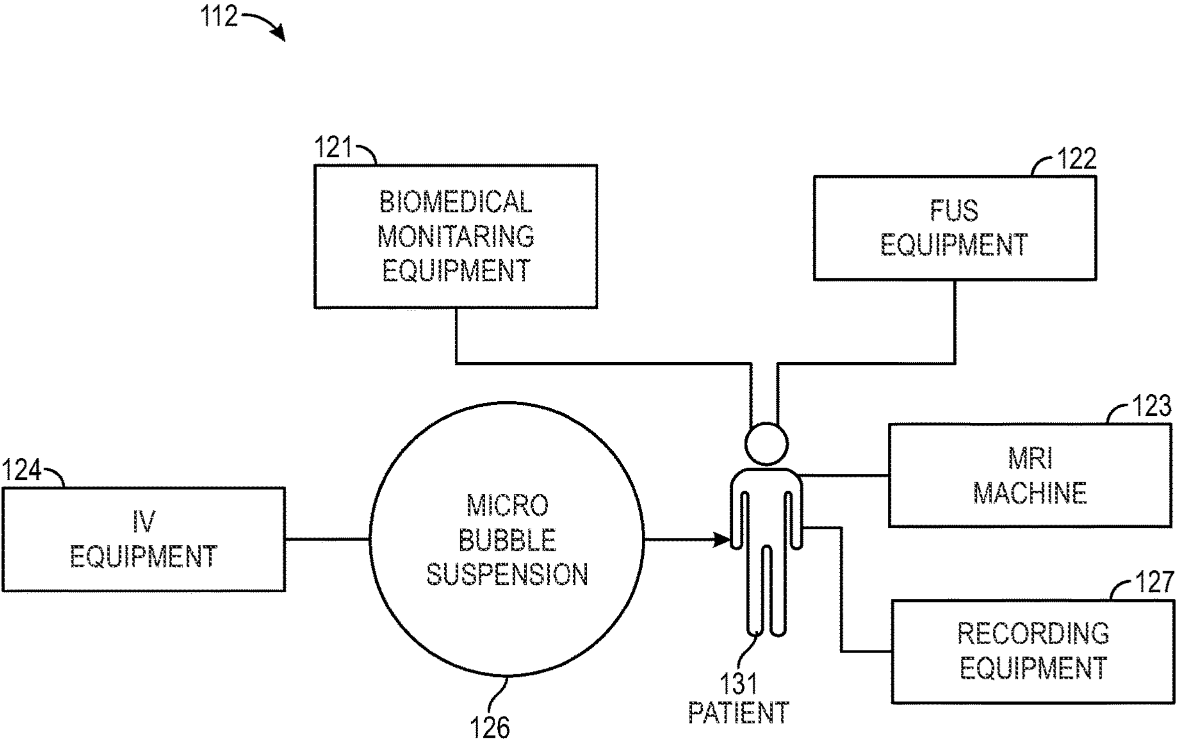
FIG. 1B depicts components in a therapy environment.

FIG. 1B depicts that therapy environment 112 can additionally include biomedical monitoring equipment 121, FUS equipment 122, MRI machine 123, IV equipment 124, and recording equipment 127. In general, IV equipment 125 can be used to administer micro bubble suspension 126 (possibly containing a psychedelic drug) to patient 131. In one aspect (and potentially in general), intranasal delivery device 101, smart aerosolization device 102, VR/AR headset 103, simulated environment 104, headphones 105 and/or speakers 106, deprivation environment 107, aromatics equipment 108, 3D modelling scanner 109, object 111, and handheld controller 113 are also included in therapy environment 112.

Components in architecture 100 and therapy environment 112 can be connected to one another over various wired and/or wireless network connections. Components in architecture 100 and therapy environment 112 can be connected to cluster 114 via WAN and/or Internet connections.

In general, psychoactive (psychedelic) drugs can be administered to patient 131 using one or more of: intranasal delivery device 101, smart aerosolization device 102, IV equipment 124, or administration.

Intranasal delivery device 101 may be provisioned from an existing drug delivery device. Various designs of intranasal delivery devices exist in the drug device industry, including but not limited Nasal delivery devices, Insufflators, Dry powder inhalers, Pressurized MeteredDose Inhalers, Breath-powered Bi-Directional technologies, Sprays and Solution, Instillation and rhinyle catheter, Compressed air nebulizers, Squeezed bottles, Metered-dose pump sprays, Single and duo dose spray devices, Nasal Cannula, ViaNase atomizers are used for administering drugs to various biological targets within the nasal cavity.

The design of intranasal delivery device 101 can address a narrow nasal valve, the complexity and convolution of the nasal geometry, together with its dynamic cyclic physiology, is idiosyncratic to each participants' physiology. The design of intranasal delivery device 101 can facilitated targeting the neuronal receptors found at the olfactory and/or trigeminal nerves. Intranasal delivery device 101 can include a variable-tip design such that an applicator tip can be interchangeable and personalized in accordance with the unique structure of a patients' nasal cavity.

Metered spray delivering between 100 μl (25-200 μl) per spray can be used, and offer high reproducibility of the emitted dose. The design of intranasal delivery device may include two or more parts: (1) interchangeable applicator tip and (2) main compartment which delivers a metered dose and accepts interchangeable liquid-drug-filled cartridges and drug transport tubing.

As described, an intranasal spray can be used to deliver a psychoactive drug to nerves in the nasal cavity. The nerves then transport the drug directly into the perivascular space in the brain. For example, intranasal device 101 can be used to deliver an intranasal spray (possibly containing a psychoactive drug) to patient 131. Drug administration via intranasal spray may provide superior blood-barrier transport of substances that are not suitable for aerosolization or IV administration. Drug administration using intranasal spray can also be utilized with augmented synergistic therapy, where psychedelic substances are accumulated in specific areas of the brain by utilizing intravenously injected microbubbles, together with focused ultrasound directed at a specific targeted brain region.

Smart aerosolization device 102 may be provisioned from an existing drug delivery device manufacturer. Smart aerosolization device 102 can heat materials to precise temperatures to reduce attrition or thermochemical conversion. Smart aerosolization device 102 can include the ability to calculate and meter the delivery of a drug in aerosolized vapor. Smart aerosolization device 102 can connect to mobile or web application software to gather data on administration. Smart aerosolization device 102 can be configured to recognize qualitative and quantitative material composition specifications, and be able to recall such data from a mobile application or computational cluster.

Smart aerosolization device 102 can be used to delivery an aerosolized psychoactive drug to patient 131's lungs that then impacts patient 131's brain. Drug administration via smart aerosolization device 102 can be remotely monitored and/or controlled by cluster 114 and a software application over various network connections. Remote monitoring and control facilitated precise dosing of psychoactive substances. Remotely generated data related to patient 131's intake is gathered by and stored within cluster 114.

Patient 131 may be able to wirelessly pair aerosolization device 102 to the software application running on their mobile device via wireless device-to-device communication (e.g., Bluetooth, wi-fi, D2D 5G, LTE Direct NFC). Pairing creates a link wherein smart aerosolization device 102 transmits sensor data to the software application and receives control commands from the software application and cluster 114. Smart aerosolization device 102's connection to the cluster 114 also enables a switch or trigger mechanism, where sensors on Smart aerosolization device 102 detect administration and automatically initiate a simulated environment 104. Simulated environment 104 can be timed based on the calculated onset times of psychedelic substances and a participant's biological factors (e.g., age, weight, BMI, etc.).

Turning briefly to FIG. 1B, IV equipment 124 can be used to intravenously administer microbubble suspension 126 containing a psychoactive drug to patient 131. Microbubble suspension 126 can be administrated into a blood vessel, for example, in patient 131's arm. FUS equipment 122 can be directed at a brain region to be treated and then engaged. FUS equipment 122 can cause microbubbles in microbubble suspension 126 to oscillate. The oscillation expands and contracts the blood vessels and the perivascular space surrounding the blood vessels. Blood vessel expansion and contraction allows a contained psychoactive drug to penetrate through the perivascular space, resulting in local accumulation of the drug at the ultrasound-targeted brain region.

In one aspect, Microbubbles (MBs) in a microbubble suspension are between one hundredth of a millimetre in diameter and micrometre in diameter. Microbubbles can be filled with gas, such as, air or perfluorocarbon. In general, microbubbles oscillate and/or vibrate when a sonic energy field is applied and may reflect ultrasound waves. Oscillation and/or vibration distinguishes the microbubbles from surrounding tissues. Microbubbles can serve as drug delivery vehicles in a variety of methods. Microbubble drug delivery methods include: (1) incorporating a drug to a lipid monolayer, (2) attaching nanoparticles and liposomes to the microbubble surface, (3) enveloping the microbubble within a larger liposome, and (4) electrostatically bonding nucleic acids to the microbubble surface.

Microbubbles used for drug delivery can serve both as drug vehicles and as a mechanism to permeate difficult to penetrate barriers, such as, the blood brain barrier. The brain is protected by tight junctions in the endothelial cell wall in the capillaries, known as the blood-brain barrier (BBB). The BBB regulates what passes into the brain from the blood, and while this function is highly desirable in healthy individuals, it also poses a barrier for therapeutics to enter the brain for cancer patients. Ultrasound has been shown to disrupt the BBB and microbubbles have been shown to assist in a temporary permeabilization. As such, ultrasound and microbubble therapy can be utilized to deliver drugs to the brain.

Intranasal delivery device 101, smart aerosolization device 102, and IV equipment 124 can be used to administer substances including, but not limited to: substances, including both naturally occurring and synthetically produced compounds, which are pharmacologically classified or considered psychoactive and/or hallucinogenic in humans can be delivered. Substances can be delivered to participants/patients intranasally, orally or intravenously in controlled environments. Delivered substances can include but are not limited to psilocin, psilocybin, 5 MEO-DMT, N, N-DMT, Baeocystin, nor-Baeocystin, Aeruginascin, Ibogaine, Voacangine, Lysergic Acid Amide, Lysergic Acid Diethylamide (LSD), Mescaline, Ketamine, 3,4-Methylenedioxyamphetamine (MDA, MDMA), 2C family drugs, 3C family drugs, Harmaline, Salvinorin A, Salvinorin B methoxymethyl ether, Salvinorin B ethoxymethyl ether, etc. Additionally, drugs from classes including but not limited to Indoles, Tryptamines, Ibogoids, Ergolines, Phenethylamines and alkoxylated phenethylamines, Substituted phenethylamines, Indane derivatives, Benzocyclobutene derivatives, NBOMe derivatives, NBOH derivatives, NBMD derivatives, NBF derivatives, Substituted amphetamines (alpha-methyl-phenethylamines), Phytocannabinoids, Synthetic cannabinoids, may be extracted from raw material sources including but not limited to plants, roots, aerial parts, branches, fungi, ergot, and other naturally occurring sources. These substances may also be synthesized or biocatalyzed, or chemically converted from other base materials. Many materials can be additionally refined, purified, or optimized in stages including but not limited to distillation, isolation, lyophilization, liposomization, emulsification, or microfluidics to render, prepare, and/or optimize the substances for human bioavailability and consumption. The material is prepared into a form factor or packaged into a delivery device designed for administering the drug in humans.

Depending on the administering device substances may be ingested orally or sublingually, absorbed transdermally, intravenously, intranasally, or via inhalation.

Devices and experiences designed to have sensory altering, augmenting, depriving, or simulating effects may support the targeting of therapeutic outcomes and reduction or elimination of negative effects of these psychoactive and hallucinogenic substances. Sensory altering, augmenting, depriving, or simulating effects of psychoactive substances can be modulated, managed, at least partially controlled, etc. by placing a patient in a simulated environment.

Returning to FIG. 1A, in general, simulated environment 104 can be facilitated using VR/AR headset 103, headphones 105 and/or speakers 106, sensory deprivation environment 107, aromatics equipment 108, 3D modelling scanner 109, object 111, therapy environment 112, handheld controller 113, cluster 114, and patient 131. VR/AR headset

103 can display simulated environment 104 or a similar distributed virtual environment to patient 131. Headphones 105 (e.g., noise canceling) and sensory deprivation environment 107 can play specific sounds to patient 131 and/or reduce noise during therapy. In one aspect, headphones 105 and/or speakers 106 playback isochronic and/or binaural audio compositions inducing brainwave states of patient 131. Aromatics equipment 108 can emit aromatics (e.g., scents) stimulating the olfactory cortex of patient 131. Patient 131 can used handheld controller 113 to interaction with simulated environment 104.

Cluster 114 can store virtual objects and code defining simulated environment 104 in programs. The virtual objects and code can be accessed via network connections to VR/AR headset 103, headphones 105 and/or speakers 106, sensory deprivation environment 107, aromatics equipment 108, 3D modelling scanner 109, and handheld controller 113. Using VR/AR headset 103 (or a projection display), optionally along with handheld controller 113, patient 131 can navigate simulated environment 104.

3D modelling scanner 109 can be custom built to specification or provisions from an existing 3D laser scanning device manufacturer. 3D modelling scanner can yield higher-accuracy point cloud data that can be modeled and used in virtual environments. For example, 3D modelling scanner 109 can be used to scan object 111 into simulated environment 104.

More specifically, cluster 114 can store virtual reality software applications designed to represent simulated objects, environment, scenarios, and objectives. The virtual reality software can be designed using graphical programming engines including but not limited to OpenVR, Unreal, and Unity, and use programming languages including but not limited to C#, and C++. The virtual reality software can utilize a graphical programming engine configured to render high-resolution graphics, with little-to-no latency, and little-to-no visual distortion of artefacts. The virtual reality software can be coded to interoperate with components of architecture 100 and therapy environment 112.

Cluster 114 may include a group of interconnected computers that work together to perform computationally intensive tasks. For example, cluster 114 can include: operating system(s), "nodes", "head nodes", "compute nodes", etc. Each node may contain one or more processors or CPUs where computation takes place. Each processor may have multiple "cores". Compute jobs may be run on a single core, or on multiple cores on one or more processors, and even on multiple nodes at one time. Nodes in each cluster are connected to one-another, for example, by high-speed, low-latency networks. The networks can support parallel operations across nodes. Database storage may also be connected to cluster 114 by, for example, high-speed, low-latency networks.

During interaction within simulated environment 104, patient 131 can be in the care of a trained therapist, medical doctor, psychologist, etc. Simulated environment 105 may be programmed to recreate a traumatic environment experienced by patient 131. By being exposed to the traumatic environment while under the care of a clinician, patient 131 can learn to reduce cognitive or emotional responses to past trauma, reduce anxiety, or reprocess circumstances and conditions which have otherwise caused distress.

Unlike traditional cognitive behavioral therapy, VR/AR-based treatment may involve adjusting simulated environment 104, such as, for example, aromatics equipment 108 adding controlled intensity smells or controlling headphones 105 to adding and adjusting sound and vibrations. Adjusting simulated environment 104 may allow the clinician to determine the triggers and triggering levels for patient 131's reactions.

Simulated environment 104 can also serve as a digital placebo, where participants in the control arm of a clinical trial are provided only the virtual reality simulation digital placebo instead of the psychoactive drug. Otherwise, the aforementioned combination of tools and technologies is used to intensify and/or modulate the effects of psychedelic therapy. In some aspects, simulation 104 and/or various modulated sensory stimuli are utilized as a digital placebo, or placebo-by-proxy. Use of a digital placebo can make it more difficult for a participant/patient to determine if they are under the influence of a psychoactive drug.

In one aspect, simulated environment 104 is a distributed virtual environment (DVEs), with interconnections between users' simulations, where users can interact with objects and other participants. Interactions can change the states of those simulated objects or other participants' sensory experiences. State change events can be transmitted to other users within the environment (e.g., within simulated environment 104) across a network or internet connection DVEs provide patients an ability to remotely participate in interactive therapy and/or group therapy simulations.

In one aspect, VR/AR headset 103 includes multiple smaller, high-resolution Organic Light-Emitting Diode (OLED) or Liquid Crystal Display (LCD) monitors (e.g., one for each human eye). The monitors provide separate images for each eye for stereoscopic graphics rendering a 3D virtual world (e.g., simulated environment 104). The monitors can also facilitate positional and rotational real-time head tracking for six degrees of movement.

Generally, VR/AR headset 103 allows patient 131 to access, view, and interact with the virtual objects (including object 111) in simulated environment 104. VR/AR headset 103 can be connected to cluster 114 and can access programs stored at cluster 114. A connection is made between VR/AR headset 103 (a projector/projection screen) via a network connection. VR/AR headset 103 (or projector/projection screen) can be synchronized with headset 105/speakers 106 and aromatics equipment 108 to provide multi-sensory coordination of visual, auditory, and olfactory stimuli during psychedelic therapy. Coordination of visual, auditory, and olfactory stimuli, can reinforce the effectiveness of the psychedelic substances. Patient 131 can also access simulated environment 104 remotely, using VR/AR headset 103 and an internet connection, for at-home psychedelic therapy sessions.

In one aspect, a mobile phone is used to display a simulated environment. A user can used a headset paired with the mobile phone to leverage existing tools and engage with the system.

Headphones 105 and/or speakers 106 are used to generate the auditory elements of a therapy session, and also to reduce or eliminate ambient noise in patient 131's physical surroundings. Headphones 105 and/or speakers 106 can connect to cluster 114 and/or VR/AR headset via wired and/or wireless network connections. As changes take place within simulated environment 104, headphones 105 and/or speakers 106 can be controlled (e.g., by cluster 114, VR/AR headset 103, etc.) to emit associated auditory creating a multisensory simulation of environments and scenarios. Headphones 105 and/or speakers 106 can also be controlled to emit isochronic or binaural audio tones and rhythmic patterns designed to further affect and/or modulate participants' neural activity.

Isochronic or binaural audio include rhythms, patterns, or frequencies and/or pattern compositions choreographed and synchronized to correspond with the visual/optical changes taking place in simulated environment 104 and various queues and/or triggers within simulated environment 104. The auditory compositions can be stored at cluster 114, available for recall during the psychedelic therapy session. Once generated, these tones and patterns are made audible through emitted sound at headphones 105 and/or speakers 106.

Frequencies and/or patterns in isochronic or binaural audio can correspond with specific regions of the brain. Modulating a psychedelic therapy experience with isochronic or binaural audio can provide a targeting effect in support of predictable, targeted therapeutic outcomes. Outcomes can be monitored using biomedical monitoring equipment 121, MRI machine 123, and possibly Internet of Things (IoT) wearable devices (e.g., fitness trackers, smart watches, pulse oximeters, etc). For example, an EEG and MRI machine 123 can be used to increase the accuracy of neural targeting. To induce the various brainwave states, isochronic or binaural audio patterns and frequencies are designed in accordance with EEG measurements. The raw EEG has usually been described in terms of frequency bands: Gamma greater than 30 (Hz), Beta (13-30 Hz), Alpha (8-12 Hz), Theta (4-8 Hz), and Delta (less than 4 Hz).

Headphones 105/speakers 106 can be synchronized with VR/AR headset 103 (or projector/projection screen) and aromatics equipment 108 to provide multi-sensory coordination of visual, auditory, and olfactory stimuli during psychedelic therapy.

Headphones 105 can be closed-backed to reduce (and possibly prevent) ambient room noise interference, and capable of generating dimensional representations of audio, such as, surround sound.

Aromatics equipment 108 can include an automated scent diffuser utilized to infuse smells into the environment during psychedelic therapy. Aromatics equipment 108 can be configured to diffuse, aerosolize, or nebulize prepared oil-water suspensions in the physical space in which the psychedelic therapy is conducted. Aromatics equipment 108 can be synchronized with VR/AR headset 103 (or projector/projection screen) and headset 105/speakers 106 to provide multi-sensory coordination of visual, auditory, and olfactory stimuli during psychedelic therapy.

3D modelling scanner 109 can scan object 111 in three dimensions and render a 3D simulation of object 111. The 3D simulation of object 111 can be placed in simulated environment 104. Patient 131 can view the 3D simulation of object 111 using VR/AR headset 103 (or projector/projection screen). Patient 131 can interact with 3D simulation of object 111 using handheld controller 113. The perceived presence of objects 111, which may be familiar, inspiring, or emotionally significant to patient 131 can modulate effects of a psychedelic substance in patient 131's body as well as reduce the risk of adverse or negative effects during a psychedelic therapy session. Object 111 can be identified during pre-screening of patient 131.

Deprivation environment 107 may be custom built to specification or provisioned from an existing floatation or sensory deprivation tank manufacturer. Sensory deprivation, sometimes called floatation or isolation therapy, can include a tank filled with water and salt solution that eliminates the brain's need to navigate gravity. In the light-free, sound-resistant, zero-gravity environment, the mind can redirect its thoughts and focus inward. In a float tank, sight and sounds are removed, with the exception of the VR headset or downward facing LED screen for displaying the virtual reality simulation. The air and water are also heated to skin temperature so it becomes difficult to know where a participant's skin ends and the water begins. Floating in a tank creates the perfect conditions for removing all external stimuli.

Patient 131 can be placed in deprivation environment 107. Deprivation environment 107 can be used to reduce (or potentially eliminate) existing ambient noise or stimulus. Reduction or elimination of ambient noise or stimulus alone can modulate a patient 131's perception. Reduction or elimination of ambient noise or stimulus also supports an environment which is free from outside influences, where the simulation environment 104 and corresponding visual, auditory, and olfactory stimuli have more affect and/or influence on patient 131.

In one aspect, deprivation environment 107 is a float tank. sensory deprivation, sometimes called floatation or isolation therapy, includes a tank filled with water and salt solution that eliminates the brain's need to navigate gravity. In the light-free, sound-resistant, zero-gravity environment, the mind can redirect its thoughts and focus inward. In a float tank, sight and sounds are removed, with the exception of the VR headset or downward facing LED screen for displaying the virtual reality simulation. The air and water are also heated to skin temperature so it becomes impossible to know where a participant's skin ends and the water begins. Floating in a tank creates the perfect conditions for removing many (and potentially all) external stimuli. Deprivation can create a dynamic of psychological "tabula rasa", which can then be controlled using any of auditory, visual, and olfactory stimuli.

Patient 131 can use handheld controller 113 to perform virtual tasks, processes, and objectives in simulated environment 104. Patient 131 can use handheld controller 113 to interact with and manipulate simulated objects (e.g., object 111) in simulated environment 104, for example, opening virtual doors, picking up or moving virtual objects, selecting trigger queues, and interacting with or completing "touchable" objectives. Patient 131 can also use handheld controller 113 to interact with other participants in a DVE, for example, shaking hands, or passing a "talking stick" during virtual group psychedelic therapy.

Computational cluster 114 can store virtual objects and code for simulated environments. 3D modeling device 109, VR/AR headset 103, headphones/speaker 106, deprivation environment 107, aromatics equipment 108, smart aerosolization device 102, IV equipment 124, biomedical equipment 1221, FUS equipment 122, MRI machine 123, recording equipment 127 and other components of therapy environment 112 can be connected to cluster 114.

Remote access to cluster 114 (e.g., participants/patients, clinicians, and clinics) can be granted via internet connection and user authorization protocols, (e.g., username and passcode, two factor authentication, etc.). Computation cluster 114 can also store natural language processing (NLP) and machine learning (ML) tools deployed in the analysis of audio, video, and clinical records data. Simulated environment 104 can also be deployed from cluster 114. Alterations to simulation code(s) constituting simulation environment 104 can be performed by accessing cluster 114 via wired or remote data transmission. Programming sequences and protocols of FUS equipment 122 and MRI machine 123 can also be stored at cluster 104 and synchronously deployed during the psychedelic therapy sessions. The timing and coordination of components used during therapy can be coordinated by central API software programs within the cluster.

Subtle vocal, semantic, or behavioral gestures and/or patterns which take place during a psychedelic substance induced therapy session(s) may be difficult (if not impossible) for human clinicians to perceive. As such, data science tools (using NLP and/or ML technologies) can analyze and process recorded video and audio files to generate structured data sets and visualizations representing the data generated from analyzed audio and video files. Processing and analysis of audio/video recordings of psychedelic therapy sessions is conducted using these data science tools, which may be deployed from cluster 114.

Data generated from the analysis can also stored at cluster 114. Generated data can be cross-referenced to chronological placement and timing of the various triggers, events, and other stimuli during a participants' experience with the virtual environments or objects, or visual, auditory, or olfactory stimuli. Multidimensional analysis provides researchers with a more detailed assessment of various responses generated during the psychedelic therapy, and a more accurate identification of which modulated elements have generated a response.

Turning again to FIG. 1B, biomedical monitoring equipment 121 and/or IoT wearable devices can include devices and tools, such as, but not limited to sensors and electrodes attached to patient 131 before, during, and after ingesting psychoactive substance in a psychedelic therapy session. Biomedical monitoring equipment 121 can include any of Functional Magnetic Resonance Imaging (fMRI) machines, Near-Infrared Spectroscopy (NIRS) machines, EEG, and EKG. Biomedical monitoring equipment 121 can monitor biometric fluctuations and gather data which can later be used to develop models of the patients 131's psychophysical effects of the substances, simulated environment 104, objects within simulated environment 104, as well as visual, auditory, and olfactory stimuli.

FUS equipment 122 may be custom built to specification or provisioned from an existing focused ultrasound (FUS) equipment. FUS equipment 122 can be used in combination with MRI machine 123 and one or more of: IV equipment 124/micro bubble suspension 126 or intranasal delivery device 101/intranasal spray to target a psychedelic substance to a region of patient 131's brain. A targeted brain region can be a brain region that is difficult to target to due to the blood-brain barrier, a brain region that is otherwise difficult to target, or a brain region where pharmacodynamics of a drug is not conducive to adequately affecting the brain region.

MRI machine 123 may be custom built to specification or provisioned from an existing MRI or fMRI equipment. MRI machine 123 can be used to monitor patient 131 before, during, and after ingesting psychoactive substance in a psychedelic therapy session. MEI machine can neural and biometric fluctuations, and gather data which can later be used to develop models of the patient 131's psychophysical effects of the substances, simulated environment 104, object in simulated environment 104, as well as visual, auditory, and olfactory stimuli. MRI machine 123 can also be used during a focused ultrasound technique further supports targeting of microbubbles of microbubble suspension 126 at specific regions of the patient 131's brain.

Recording equipment 127 (e.g., audio/video recording equipment) can be used to monitoring patient 131's behavior, spoken words, vocal patterns before, during, and after the ingestion of a psychedelic substance. Recording equipment 127 can be used for recording patient 131's psychedelic therapy sessions. Recordings can then be processed using data mining tools, including but not limited to ML, deep learning, and NLP, which clinicians deploy from cluster 114. These data science tools analyze and process the raw video and audio files to create structured and collated data sets, and visualizations which represent the analyzed audio and video files. Using these tools, clinicians are able to detect, observe, and analyze behavioral and semantic anomalies otherwise unperceivable by a human. Recording equipment 127 can be configured to record dimensional sound and video in 360 degrees.

Aspects of the invention may also integrate haptic vibration packs. A participant/patient cab wear one or more haptic vibration packs as a vest and function to deliver the perception of sound. Haptic technology, also known as kinaesthetic communication or 3D touch, refers to any technology that can create an experience of touch by applying forces, vibrations, or motions to the user. Haptic devices may incorporate tactile sensors that measure forces exerted by the user on the interface. Vibration packs can be connected to cluster 114. Vibration packs can be synchronized with VR/AR headset 103 (or projector/projection screen), headphones 105/speakers 106, and aromatics equipment 108 to provide multi-sensory coordination of visual, auditory, and olfactory stimuli during psychedelic therapy.

Aspects of the invention can be implemented within as well as outside of a clinical environment. Within a clinical environment, researchers, behavioral psychologists and/or psychiatrists are present for and participate in pre-screening, preliminary evaluations, during psychedelic therapy sessions, and post therapy evaluations, while facilitating behavioral therapy during each phase. Clinicians prepare and/or administer psychedelic drugs using intranasal or aerosolization devices or IV administration. Clinicians can also prepare simulated environment 104, scan object 11, and prepare equipment for use on patient 131 and by patient 131. Clinicians can also engage and monitor biomedical monitoring equipment 121 and activate recording equipment 127. Clinicians can also curate and analyze various data generated during natural language processing and machine learning processing. Clinicians may also wear and/or utilize VR/AR headset and a handheld control to directly engage with patient 131 in simulated environment 104.

Clinicians can be trained in various modalities of behavioral therapy, psychiatry, and mental health care. Clinicians can be familiar with or trained in subject matter areas including but not limited to psychedelics, PK/PD, biomedical sciences, pharmaceutical sciences, data science, machine learning, chemistry, pharmacology, neuropharmacology, psychedelic medicine, spirituality, mysticism, theology, compassion, empathy, trauma, consciousness, psychology, best practices, GLP, LIMS, and emergency medicine. Clinicians can diagnose, prepare and administer drugs, engage technologies, conduct pre & post care research, coordinate data management, and effectively interact with participants.

Outside a clinical environment, aspects of the invention can facilitate psychedelic or psychoactive drug use. Using owned or leased personal VR/AR headsets and accessory equipment, participates can remotely access simulated environments (e.g., simulated environment 104) and DVEs. The VR/ASR headsets can be coordinated with at-home auditory and/or olfactory modulating systems.

Example Treatment Process

A participant/patient meets with clinicians to determine appropriate drugs and care pathway. The clinicians supervise a series of baseline analyses of the participant/patient to assess the participant/patient's current health. For example, the patient/participant may be diagnosed with major depressive disorder (MDD), generalized anxiety disorder (GAD), post-traumatic distress disorder (PTSD), etc. The clinicians can select psychoactive agents/drugs to address conditions identified in the baselines analyses. Different psychoactive agents/drugs (or combinations thereof) and psychoactive agent/drug administration mechanisms may be more appropriate for different conditions. The clinicians can tailor psychoactive agents/drugs selection and administration mechanisms to address identified heath issues, conditions, etc.

A 3D scanner can be used to scan participant/patient's object into a simulated environment.

Participant/patient and clinician can conduct psychological preparation during the days/weeks prior to VR/AR psychedelic therapy session(s). Simulations can be selected, planned, staged, designed per participant/patient's needs/goals, identified health issues, conditions, etc. For example, simulations can be targeted to treat major depressive disorder (MDD), generalized anxiety disorder (GAD), post-traumatic distress disorder (PTSD), etc.

Participant/patient attends VR psychedelic drug therapy session. Clinicians prepare room, materials, and participant/patient begins session. Equipment is connected and headset secured on participant/patient head/face.

If/when appropriate, microbubbles are injected intravenously. A selected psychoactive agent or drug (or combination thereof) is administered to the participant/patient using selected administration mechanisms (e.g., via intranasal, intravenously, inhalation, oral ingestion). Simulations can be commenced and timed to calculated/observed drug onset of action. Participant/patient engages in virtual environment, completes tasks, and interacts within DVE group.

Clinicians manage session, engage in guidance methods and/or psychotherapy. Clinicians taking record, monitoring recording equipment, ID peak of action.

Simulation(s) can be timed to deliver climax of sensory modulation during peak of drug action. Sensory modulation(s) (e.g., visual, auditory, olfactory) continues for duration of drug action. Clinicians observe and record various data points. Clinicians observe, determine drug action termination. Participant/patient verbally confirms drug action termination. Clinicians end simulations and/or sensory modulation, remove headset. Participant/patient and Clinician engage in post-therapy processing session & evaluation. Session ends.

Participant/patient is authorized for remote access to cluster and virtual environments. Participant/patient may lease/rent/purchase compatible VR/AR equipment for at-home use. Participant/patient returns for follow-up psychedelic drug therapy and/or psychotherapy session(s). Participant/patient engages in at-home psychedelic drug therapy and/or remote psychotherapy session(s)

Ongoing research is conducted using audio/video recordings and biometrics. NLP & machine learning models/data can be utilized to develop large-scale data sets and adaptive, predictive deep-learning and/or A.I. models or experiences/results. Models and data utilized to optimize/improve drug(s), simulations, modulations, etc.

The present described aspects may be implemented in other specific forms without departing from its spirit or essential characteristics. The described aspects are to be considered in all respects only as illustrative and not restrictive. The scope is, therefore, indicated by the appended claims rather than by the foregoing description. All changes which come within the meaning and range of equivalency of the claims are to be embraced within their scope.

What is claimed:

1. A method comprising:

administrating a psychoactive agent to a patient;

receiving virtual environment code from a cluster;

executing the virtual environment code while the patient is under the influence of the psychoactive agent, including:

simulating a patient virtual environment including visual stimuli, auditory stimuli, and olfactory stimuli;

presenting the patient virtual environment to the patient, including the visual stimuli, auditory stimuli, and olfactory stimuli, using one or more hardware devices;

modulating the visual stimuli, the auditory stimuli, and the olfactory stimuli within the patient virtual environment to induce a specific patient response; and presenting the patient virtual environment to the patient again, including the modulated visual stimuli, modulated auditory stimuli, and modulated olfactory stimuli, using the one or more hardware devices.

2. The method of claim 1, further comprising utilizing sensory deprivation of the patient prior to executing the virtual environment code.

3. The method of claim 1, further comprising emitting isochronic or binaural tones through an audio device, included in the one or more hardware devices and worn by the patient.

4. The method of claim 1, wherein modulating the visual stimuli, auditory stimuli, and olfactory stimuli within the patient virtual environment comprises emitting a sound through an audio device.

5. The method of claim 1, wherein modulating the visual stimuli, auditory stimuli, and olfactory stimuli within the patient virtual environment comprises emitting a scent at aromatics equipment.

6. The method of claim 1, wherein simulating the patient virtual environment comprises simulating a distributed virtual environment (DVE).

7. The method of claim 1, wherein executing the virtual environment code comprises including a 3D digital representation of an object associated with the patient in the patient virtual environment.

8. The method of claim 1, wherein administrating the psychoactive agent to the patient comprises administering the psychoactive agent via one of: intranasal, inhalation, oral ingestion, or intravenously.

9. The method of claim 1, further comprising:

injecting microbubbles into the patient;

controlling focused ultrasound (FUS) equipment to move the microbubbles to accumulate the psychoactive agent in a targeted brain region of the patient.

10. The method of claim 1, wherein modulating the visual stimuli, the auditory stimuli, and the olfactory stimuli within the patient virtual environment to induce the specific patient response comprises modulating the visual stimuli, the auditory stimuli, and the olfactory stimuli within the patient virtual environment to induce a specific patient therapeutic outcome.

11. The method of claim 1, wherein modulating the visual stimuli, the auditory stimuli, and the olfactory stimuli within the patient virtual environment to induce the specific patient response comprises modulating the visual stimuli, the auditory stimuli, and the olfactory stimuli within the patient virtual environment to induce a specific patient psychophysical outcome.

12. The method of claim 1, wherein presenting the patient virtual environment to the patient, including the visual stimuli, auditory stimuli, and olfactory stimuli, using one or more hardware devices comprises presenting auditory cortex simulation introducing various audible tones and rhythms during a psychedelic, or simulated psychedelic, therapy session.

13. The method of claim 1, wherein presenting the patient virtual environment to the patient, including the visual stimuli, auditory stimuli, and olfactory stimuli, using one or more hardware devices comprises presenting a soundscape or specific sonic frequencies associated with one or more of: a specific brain wave state, a state of consciousness, or a psychophysical response, tailored to support a therapeutic outcome.

14. The method of claim 1, wherein presenting the patient virtual environment to the patient, including the visual stimuli, auditory stimuli, and olfactory stimuli, using one or more hardware devices comprises presenting the patient virtual environment to the patient obfuscating whether the patient is in a control arm of a clinical trial or in a drug arm of the clinical trial.

15. A method comprising:

administrating a psychoactive agent to a patient;

receiving virtual environment code from a cluster;

executing the virtual environment code while the patient is under the influence of the psychoactive agent, including:

simulating a distributed virtual environment including visual stimuli, auditory stimuli, and olfactory stimuli for the patient and including visual stimuli, auditory stimuli, and olfactory stimuli for one or more other participants;

presenting the distributed virtual environment to the patient, including the visual stimuli, auditory stimuli, and olfactory stimuli, using one or more hardware devices, wherein one or more of the visual stimuli, auditory stimuli, and olfactory stimuli are presented based on actions of the one or more other participants having previously been presented the visual stimuli, auditory stimuli, and olfactory stimuli using the one or more hardware devices;

modulating the visual stimuli, the auditory stimuli, and the olfactory stimuli within the distributed virtual environment based at least in part on the actions of the one or more other participants; and presenting the distributed virtual environment to the patient, including the modulated visual stimuli, modulated auditory stimuli, and modulated olfactory stimuli, using the one or more hardware devices.

16. The method of claim 15, wherein at least one of the one or more other participants is a clinician supervising a psychedelic assisted therapy session of the patient.

17. The method of claim 15, wherein the one or more other participants are part of interactive group therapy during a psychedelic assisted therapy session.

* * * * *